United States Patent [19]

Typpo

[11] Patent Number: 4,789,431
[45] Date of Patent: Dec. 6, 1988

[54] APPARATUS FOR SENSING THE THICKNESS OF A PULP SUSPENSION ON THE FORMING WIRE OF A PAPER MACHINE

[75] Inventor: Pekka Typpo, Cupertino, Calif.

[73] Assignee: Impact Systems, Inc., San Jose, Calif.

[21] Appl. No.: 80,327

[22] Filed: Jul. 31, 1987

[51] Int. Cl.[4] ............... D21F 7/06; G01N 29/00
[52] U.S. Cl. ............... 162/263; 73/629; 73/632; 162/252
[58] Field of Search .......... 162/49, 198, 263, 252, 162/258, 259; 73/627, 628, 629, 632, 634; 356/244; 350/632, 530

[56] References Cited

U.S. PATENT DOCUMENTS

| | | | |
|---|---|---|---|
| 2,743,429 | 4/1956 | Endman et al. | 73/634 |
| 3,442,756 | 5/1969 | Lehtinen | 162/198 |
| 3,485,088 | 12/1969 | O'Connor | 73/629 |
| 3,574,624 | 3/1986 | Lehtinen et al. | 162/198 |
| 4,402,604 | 9/1983 | Nash | 162/49 |
| 4,470,307 | 9/1984 | Genter | 73/634 |

FOREIGN PATENT DOCUMENTS 249727  8/1969  U.S.S.R. ............... 73/629

*Primary Examiner*—Steve Alvo
*Attorney, Agent, or Firm*—Flehr, Hohbach, Test, Albritton & Herbert

[57] ABSTRACT

Apparatus for sensing the thickness of a pulp suspension, having zones or slices, on the forming wire of a paper making machine includes an array of ultrasonic transducers located in the apertures of a structural member mounted in a cross-direction under the forming wire near the headbox of the machine. Each ultrasonic transducer is mounted on a flexible sheet which is mounted to an aperture and the transducer moved into close proximity to the bottom of the forming wire by means of air pressure in the structural member. A second array of transducers downstream of the first can be utilized for diagnostics.

7 Claims, 4 Drawing Sheets

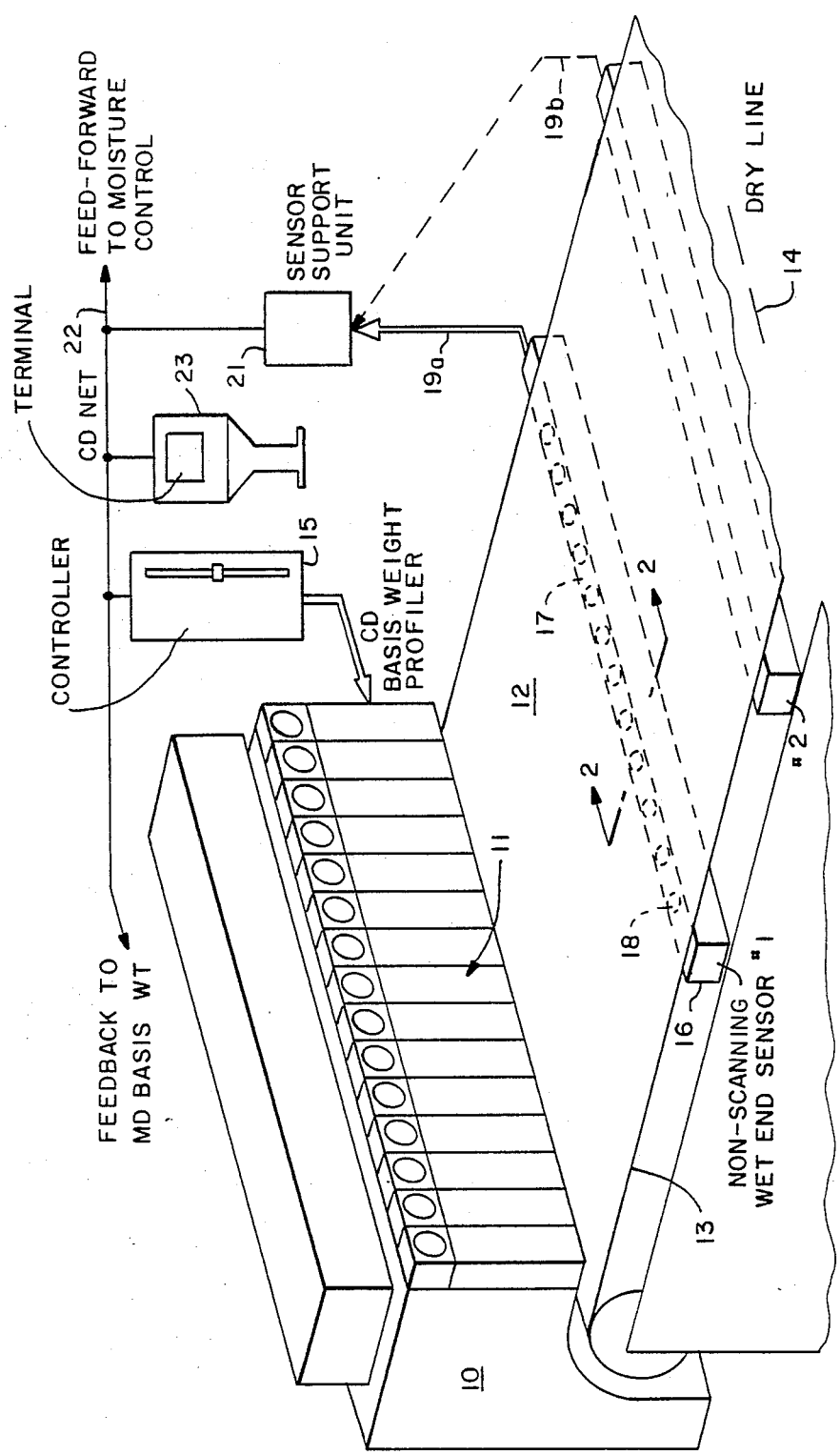
FIG.—1

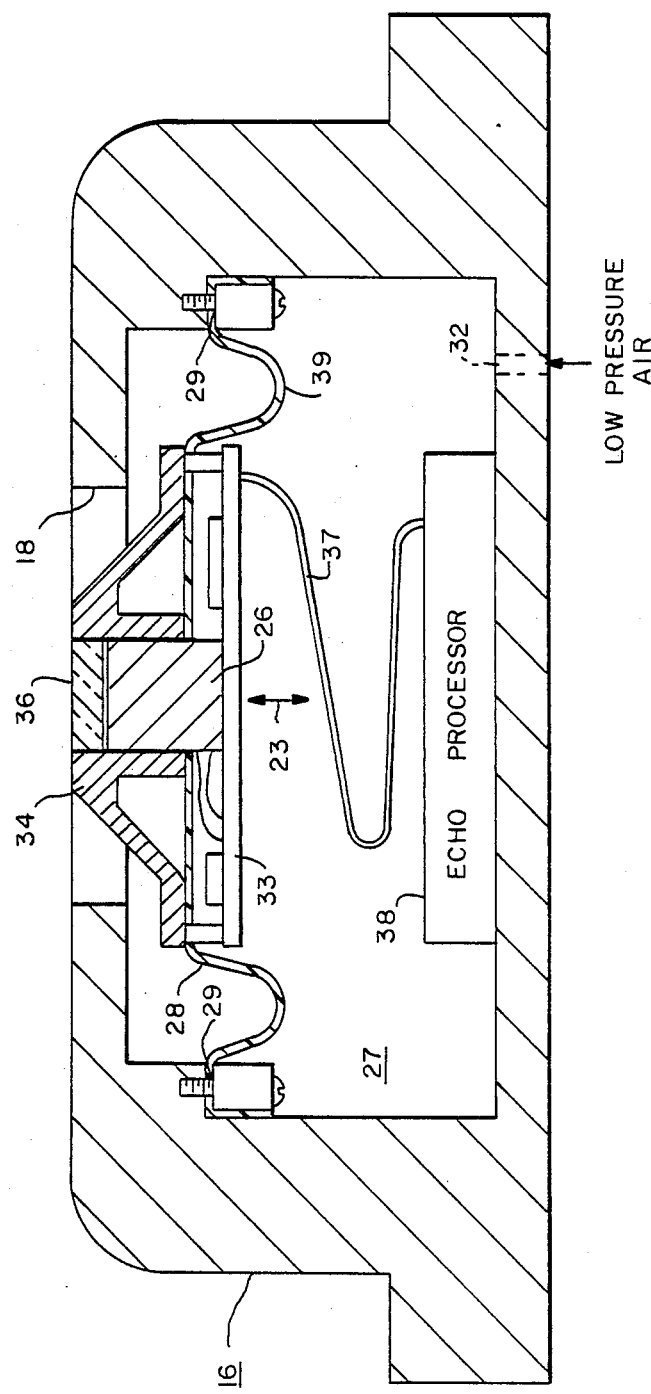
FIG.—2

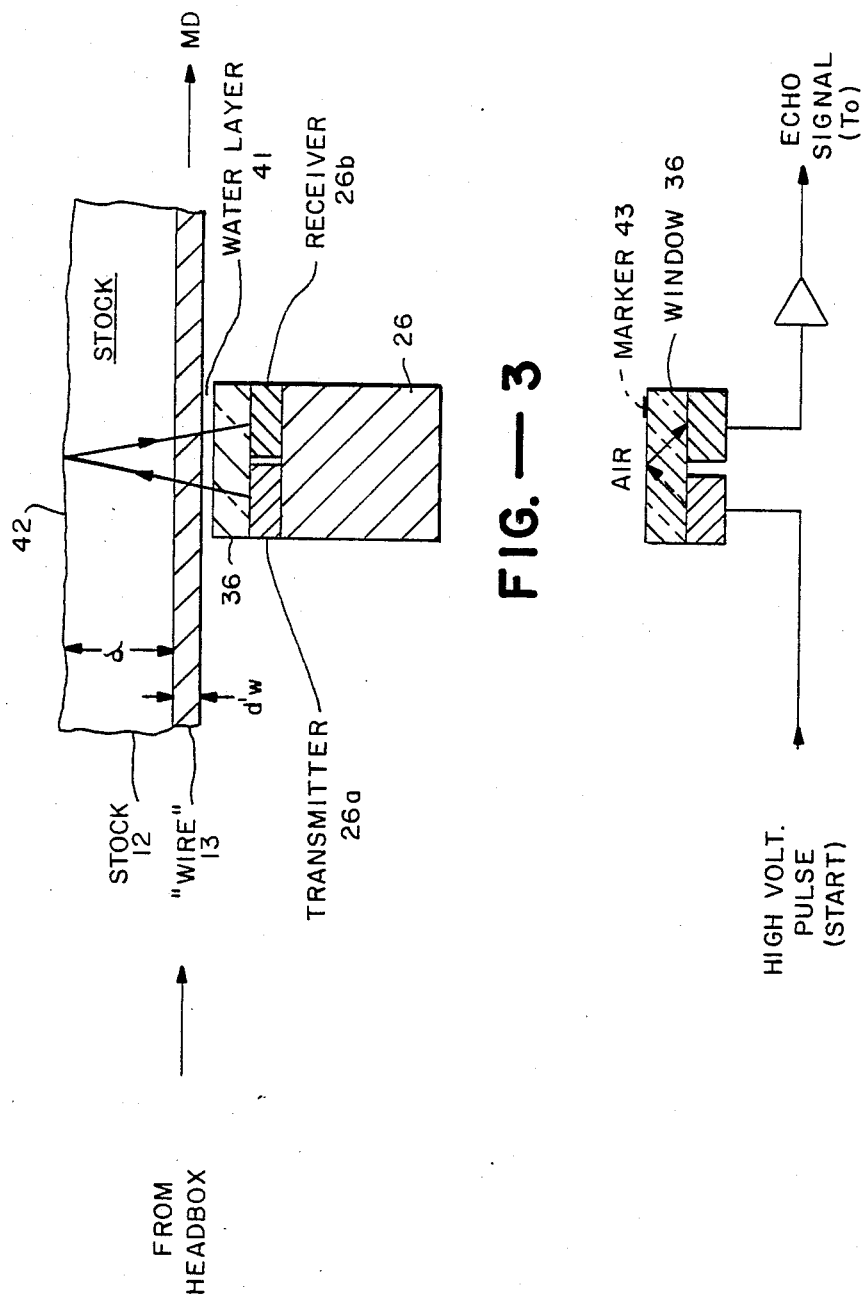

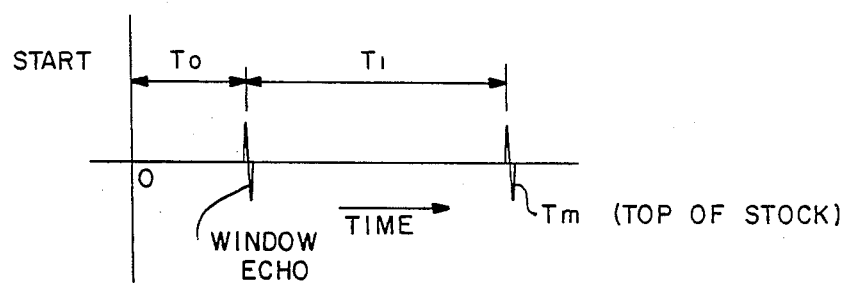
FIG.—5
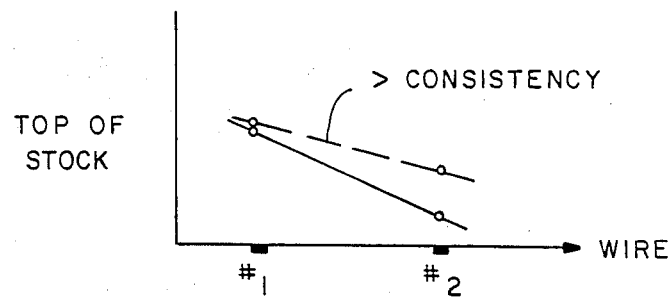
FIG.—6A
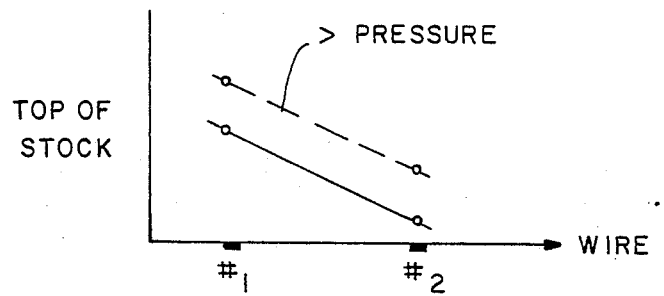
FIG.—6B

4,789,431

APPARATUS FOR SENSING THE THICKNESS OF A PULP SUSPENSION ON THE FORMING WIRE OF A PAPER MACHINE

BACKGROUND OF THE INVENTION

The present invention is directed to an apparatus for sensing the thickness of a pulp suspension course on the forming wire of a paper machine and more particularly, to an apparatus which includes an array of ultrasonic transducers. Lehtinen U.S. Pat. No. 3,442,756 discloses a method of measuring the thickness of pulp suspension being manufactured on the forming wire of a paper machine by the use of an ultrasonic transducer. A single transducer is put under the forming wire of a machine with the water running through the wire acting as an acoustic connector.

With improved high speed actuators for correcting short-term variations in moisture, both in the cross-direction and machine direction of the paper being manufactured, a real time non-scanning wet end sensor is desirable. The Lehtinen sensor, as very cursorily illustrated in the patent, was suitable only for a "probe" operation on a test basis where only a single reading at a time was taken. Also, no scanning of the sensor was suggested, although this is still impractical since a scanning delay cannot be tolerated for correction of short-term variations in moisture and basis weight.

OBJECTS AND SUMMARY OF INVENTION

It is therefore a general object of the present invention to provide improved apparatus for sensing the thickness of a pulp suspension course on the forming wire of a papermaking machine.

It is a more specific object to provide a non-scanning wet end sensor.

In accordance with the above objects, there is provided an apparatus for sensing the thickness of a pulp suspension, having zones or slices, on the forming wire of a papermaking machine during operation of the machine comprising elongated structural means having a length corresponding to the cross-directional (CD) width of said suspension and having a top face with a plurality of apertures, mounted in said cross-direction in proximity to the side of said forming wire opposite said pulp suspension, each of said apertures of said top face corresponding to a zone or slice.

Ultrasonic transducer transmit and receive means are located at each said aperture.

Flexible sheet means are mounted to each aperture and carry window means for the transducer means.

Means are provided for moving the sheet means and window into close proximity to said wire.

BRIEF DESCRIPTION OF DRAWINGS

FIG. 1 is a perpsective view of a papermaking machine embodying the present invention and associated block diagram.

FIG. 2 is a cross-sectional view taken along line 2—2 of FIG. 1.

FIG. 3 is a simplified cross-sectional view of a portion of FIG. 2, showing the apparatus of the invention in actual use on the machine of FIG. 1.

FIG. 4 is a simplified cross-section of a portion of FIG. 3 illustrating a zeroing step.

FIG. 5 is a timing diagram illustrating the operation of the invention.

FIGS. 6A and 6B are graphs illustrating an alternate embodiment of the invention.

DESCRIPTION OF PREFERRED EMBODIMENTS

FIG. 1 illustrates the wet end sensor of the present invention on a paper making machine which includes a head box 10, which by means of slice controls indicated at 11 across the various, for example, 3 inch zones or slices, produces a pulp suspension 12 on a forming wire 13. This pulp suspension 12 is, of course, highly liquid with paper pulp being suspended in it. Slice control 11 is automated so that each 3" slice of the pulp suspension 12 may be controlled remotely by means of a controller 15. Thus, this combination may be termed a cross-direction basis weight profiler.

As is well known in paper making technology, the pulp suspension 12, as it moves down the wire, loses water content and eventually a dry line 14 occurs.

In accordance with the present invention, a non-scanning wet end sensor indicated by #1, and also an additional downstream sensor #2, each includes an elongated structural member 16 which extends across the width of suspension 12 in a cross-direction. A suitable mounting is provided for the structural member. Member 16 has a top face indicated at 17 which is in close proximity to the bottom of wire 13 (the opposite side as that on which the suspension 12 is located) with apertures 18, each corresponding to a zone or slice of the headbox 10. Located in conjunction with each aperture 13 and structural member 16 is an ultrasonic sensing device which senses the thickness of suspension 12 in that location. This is done for each of the apertures 18 across the entire width of the paper suspension 12 in real time.

Such information is communicated via the links 19a and 19b to a sensor support unit 21 and thence to a cross-direction communication network line 22. This information is displayed on a terminal 23 and, as discussed above, may control the cross-direction basis weight profiler by means of controller 15, provide a feedback for control of machine direction basis weight (which may be, for example, a pressure valve on headbox 10) and in addition may provide for feed forward moisture control on communications line 22 to a gas or electric heater type feed forward moisture control unit. Such a unit is shown in U.S. Pat. No. 4,573,402 assigned to the present assignee. And the cross-direction basis weight profiler is sold commercially by the assignee under the trademark "DYNA-FLEX."

FIG. 2 illustrates in detail a cross-section of elongated structural member 16 showing the preferred embodiment of an ultrasonic sensor 26 for sensing the thickness of the pulp suspension 12 in a particular zone or slice.

Thus, the transducer 26 being located at the aperture 18 illustrates one of the several apertures in a cross direction across pulp suspension 12 which corresponds to the various zones or slices of the pulp suspension. It is obvious, of course, that depending on the type of pulp or paper being manufactured, for example, newsprint versus liner board, that fewer transducers may be necessary. In any case, the only criterion is that they are fixed (as opposed to scanning) in order to give an immediate real time signal on which an actuator may change a parameter of basis weight or moisture of the paper being manufactured.

The elongated structural member 16 typically can be a single metal beam having an inner cavity 27. Ultrasonic transducer 26 in this present embodiment is suspended on a flexible sheet member 28, of, for example, rubber, which is disc-like, mounted at its edge 29 to the structural member 16, to provide an airtight and liquid tight seal forming chamber 27. Thus, the admission of low pressure air through the aperture 32 by means of an associated pressure pump (not shown) will cause the flexible sheet to move in the directions of the double-ended arrow 33, either to or away from close proximity with the wire 13. (See also FIG. 3.)

As illustrated in FIG. 2, transducer 26 is mounted to a platform 33 containing, for example, a preamplifier, and the platform is clamped by means of an annular unit 34 to flexible sheet 28. On the top face of the ultrasonic transducer 26 is a window 36 through which the ultrasonic pulses as generated by transducer 26 may easily pass. In the preferred embodiment, the window may be plexiglass, which has an acoustic velocity very close to that of water. Then an electrical cable 37 connects to more sophisticated electronics unit 38 designated echo processor. This unit is then connected by a common cable, referring now to FIG. 1, to the sensor support unit 21.

Although the ultrasonic transducer 26 is shown in contact with window 36 and movable as a single unit, the transducer 26 can be fixed with merely the window or some other suitable aperture moving toward the bottom of wire 13. And then the flexible sheet material 28 can be arranged so that the remainder of the cavity is kept dry but there is still a water interface between the window 36 and the transducer 26. The water interface is necessary since the ultrasonic pulses reflect mainly on an interface between water and, for example, air which has a significantly different acoustic transmission property.

The sheet material 28 in the preferred embodiment of FIG. 2 covers the aperture 18 to isolate the interior 27 of the structural member 26 from ambient conditions and thus to maintain the electrical components such as echo processor 38 isolated from the water, heat and humidity of the forming wire. In addition, the chamber 27 allows the air pressure actuation of the transducer 26 into close proximity with the bottom of wire 13. Alternatively, of course, other techniques for moving the sheet could be utilized, including a mechanical plunger.

Also in the preferred embodiment of FIG. 2 the sheet means 28 has a single annular corrugation 39 which provides for a fairly rigid mounting of transducer 26 and its associated components but allows sufficient flexibility to move the entire assembly into proximity with the wire with relatively low air pressure; typically, a fraction of a psi.

FIG. 3 illustrates the operation of the transducer 26 as it is placed in close proximity to the bottom of wire 13. In actual practice wire 13 is formed of a plastic material: then the paper pulp suspension is indicated with the pulp suspended within the water layer. This has a thickness of "d," which is the measurement to be provided by the ultrasonic transducer 26. This transducer is commercially available, for example, from the Krautkramer Branson Company of Lewistown, Pa. It is a piezoelectric crystal which has semicircular halves having a transmitter portion 26a and a receiver portion 26b. These are well known for sensing distances. An ultrasonic pulse passes through the widow 36, the associated water layer 41 through the wire 13 and then to the top of the stock designated 42. There, because of the water air interface, it is reflected and the transit time of the pulse thus indicates the distance of the transducer from the top 42 of the pulp suspension 12. Wire 13 has a known thickness, of course, which has been designated $d_w'$. Water layer 41 provides a continuity of the transmission of the ultrasonic pulse without any acoustic interfaces since the plexiglass window 36 has an acoustic impedance similar to water.

FIG. 5 illustrates the acoustic echoes that are received. In operation there is a high energy, high voltage start pulse generated by transducer 26 and transmitter 26a. This is a time $T_0$. Thereafter, as illustrated in FIG. 4, if the transducer is in the lowered position and no water is present, the air-window interface illustrated in FIG. 4 will produce the window echo at a time $T_0$. This is one way of zeroing the instrument. Then the top of the stock 42 produces, as illustrated in FIG. 5, a pulse time $T_m$. Thus, it is obvious as shown in equation 1, infra, that the time $T_1$ is equal to the top of the stock measurement minus the window echo.

And as further illustrated in equation 1, the transit time $T_1$ is a measure of the stock thickness d and the thickness of the wire $d_w$. However, since the wire is made of plexiglass material, as shown in equation 4, a compensation must be made between the velocity of wire and water. Then, finally, in equation 3, the distance d is computed by use of the time $T_1$ with the effective wire thickness, after it has been compensated, subtracted therefrom.

There are other techniques for zeroing, as briefly mentioned above, where rather than the entire ultrsonic transducer 26 moving into close proximity to the bottom of wire 13, only a window 36 would move toward the wire with the transducer being fixed. Here, as illustrated in FIG. 4, since the window would be at a significantly different location, to zero on the window and measure its location, a metal marker 43 might be utilized. And of course this marker 43 could be used even if the transducer were integral with the window 36.

In any case, the manipulation of the transducer pulses is well known in the art.

An alternative embodiment of the invention which has already been illustrated in FIG. 1 is the use of an additional array of fixed wet end sensors designated as #2 located downstream from the #1 set of sensors toward the dry line 14. This arrangement gives an opportunity for diagnostics by measuring consistency or pressure variations as illustrated in FIGS. 6A and 6B, respectively. For example, in FIG. 6A, the top of the stock measurement is indicated for the wet end sensor array No. 1 and wet end sensor array No. 2. The dashed curve is the curve later in time. Thus, if the curve of thickness is the same at the earlier sensor in time but then has changed at the later further downstream sensor No. 2, this means greater consistency is present in the pulp. This is because the rate of drainage has been affected.

And referring to FIG. 6B, if the later dashed line in time is parallel to the earlier, it indicates there was no consistency change but a pressure upset. Such a pressure variation may be due to control instabilities, pulsations of screens and pumps or mechanical vibrations. On the other hand, consistency variations may not only be due to control instabilities but also to flow variations, level variations or poor mixing. Thus, the comparing of signals from the two sets of ultrasonic transducers—one located downstream from the other—aids in distinguishing between pressure surges and consistency variations and is in general a diagnostic aid.

Thus, an improved apparatus for sensing the thickness of a pulp suspension on a forming wire has been provided.

Equations $$T_1 = T_m - T_o \quad (1)$$

$$\frac{2(d + d_w)}{T_1} = v \text{ (velocity of sound in water)} \quad (2)$$

$$d = 1\frac{vT_1}{2} - d_w \quad (3)$$

$$d_w = d'_w \frac{(v\text{water})}{(v\text{wire})} \quad (4)$$

I claim:

1. Apparatus for sensing the thickness of a pulp suspension, having zones on the forming wire of a papermaking machine during operation of the machine comprising:

an elongated hollow structural member having a length corresponding to the cross-directional (CD) width of said suspension and having a top face with a plurality of apertures, mounted in said cross-direction in proximity to the side of said forming wire opposite said pulp suspension, each of said apertures of said top face corresponding to one of said zones on the forming wire;

ultrasonic transducer means for transmitting and receiving ultrasonic pulses located at each said aperture;

a flexible sheet mounted across each aperture and carrying a window for said ultrasonic transducer means and forming a substantially airtight chamber with said hollow structural member;

and air pressure means having a source of compressed air and fluidly connected to said air tight chamber for moving said sheet and said window into close proximity to said wire.

2. Apparatus as in claim 1 wherein said transducer means is integrally mounted to said window.

3. Apparatus as in claim 1 wherein said flexible sheet covers said apertures to isolate the interior of the structural member from ambient conditions.

4. Apparatus as in claim 1 where said window transmits sound with a velocity substantially similar to that of water.

5. Apparatus as in claim 1 where said flexible sheet has at least one annular corrugation.

6. Apparatus as in claim 1, together with an additional elongated structural member, having a plurality of associated ultrasonic transducer means located in a cross-direction downstream from the first structural member but before a dry line of said pulp suspension.

7. Apparatus as in claim 6, including means for comparing signals from the ultrasonic transducers of said additional elongated structural member with said first structural member for distinguishing between pressure surges from a head box producing said pulp suspension and consistency variations thereof.

* * * * *